United States Patent [19]

Singh et al.

[11] Patent Number: 5,408,999
[45] Date of Patent: Apr. 25, 1995

[54] FIBER-OPTIC PROBE FOR THE MEASUREMENT OF FLUID PARAMETERS

[75] Inventors: Raghuvir Singh; Leslie A. Schlain, both of The Woodlands, Tex.

[73] Assignee: Optex Biomedical, Inc., The Woodlands, Tex.

[21] Appl. No.: 252,906

[22] Filed: Jun. 2, 1994

Related U.S. Application Data

[63] Continuation-in-part of Ser. No. 965,193, Oct. 23, 1992, abandoned.

[51] Int. Cl.$^6$ .............................................. A61B 5/00
[52] U.S. Cl. ..................................... 128/634; 436/68; 436/136; 436/172
[58] Field of Search ................................ 128/633–634, 128/632, 637; 422/82.06–82.07; 436/68, 133, 136, 163; 356/402, 409–411

[56] References Cited

U.S. PATENT DOCUMENTS

| | | | |
|---|---|---|---|
| 3,904,373 | 9/1975 | Harper | 252/408 X |
| 4,200,110 | 4/1980 | Peterson et al. | 128/634 |
| 4,752,115 | 6/1988 | Murray et al. | 350/96.29 |
| 4,785,814 | 11/1988 | Kane | 128/634 |
| 4,824,789 | 4/1989 | Yafuso et al. | 436/68 |
| 4,889,407 | 12/1989 | Markle et al. | 350/96.29 |
| 4,919,891 | 4/1990 | Yafuso et al. | 422/58 |
| 4,974,929 | 12/1990 | Curry | 350/96.29 |
| 5,000,901 | 3/1991 | Iyer et al. | 264/299 |
| 5,005,576 | 4/1991 | Gunther | 128/634 |
| 5,006,314 | 4/1991 | Gourley et al. | 422/82.07 |
| 5,043,285 | 8/1991 | Surgi | 436/136 |
| 5,047,208 | 9/1991 | Schweitzer et al. | 128/634 X |
| 5,054,882 | 10/1991 | Riccitelli et al. | 385/12 |
| 5,094,959 | 3/1992 | Allen et al. | 436/172 |
| 5,098,659 | 3/1992 | Yim et al. | 422/82.07 |
| 5,102,625 | 4/1992 | Milo | 422/82.07 |
| 5,115,811 | 5/1992 | Hartlaub et al. | 128/634 |
| 5,124,130 | 6/1992 | Costello | 422/82.06 |
| 5,127,077 | 6/1992 | Iyer et al. | 128/634 X |
| 5,133,032 | 7/1992 | Salter et al. | 385/60 |
| 5,143,066 | 9/1992 | Kohives | 128/634 |
| 5,152,287 | 10/1992 | Kane | 128/634 |
| 5,159,654 | 10/1992 | Salter | 385/59 |
| 5,219,527 | 6/1993 | Hui et al. | 128/634 X |
| 5,251,633 | 10/1993 | Wunderling et al. | 128/634 |

OTHER PUBLICATIONS

"A Fiber–Optic pH Sensor Using Acid-Base Indicators Covalently Bound on Controlled Pore Glass", Baldini et al., SPIE Proceedings, vol. 1587 (1991).
"Reusable Glass-Bound pH Indicators", Harper, Analytical Chemistry, vol. 47 (1975).
"Continuous Arterial Blood Gas Monitoring in Rabbits: An Efficient Method for Evaluation of Ratio Based Optrodes", Martin et al., SPIE, vol. 1648 (1992).
"Design and Applications of Highly Luminescent Transition Metal Complexes", Demas and DeGraff, Analytical Chemistry, vol. 63, (1991).
"Biologically Inert Synthetic Dural Substitutes", by Sakas et al., J. Neurosurg, vol. 73 (1990).
"Determination of Oxygen concentration by Luminescence Quenching of a Polymer–Immobilized Transition-Metal Complex", Demas et al., Analytical Chemistry, vol. 59 (1987).
"Photophysics and Photochemistry of Oxygen Sensors Based on Luminescent Transition-Metal Complexes", Demas et al., Analytical Chemistry, vol. 63 (1991).
"Fiber Optic pH Probe for Physiological Use", Peterson et al., Analytical Chemistry vol. 52 (1980).

*Primary Examiner*—Angela D. Sykes

[57] ABSTRACT

A fiber optic sensor suitable for measuring and monitoring fluid parameters, e.g. blood parameters such as carbon dioxide and oxygen partial pressure and hydrogen ion concentration ( pH ). Analyte sensitive chemistry in such probes includes molecules sensitive to responding to an analyte change in an optically detectable system. Methods of making analyte measuring chemistries including disposing an indicator complex in the path of light and casting over it films of permeable / semipermeable polymer membranes capable of diffusion of gases and other analytes. A liquid control validation solution ) acts as a simulating standard for blood gas analysis. Liquid calibration solutions which mimic fluids such as blood to validate and test sensors for long term stability.

10 Claims, 1 Drawing Sheet

FIBER-OPTIC PROBE FOR THE MEASUREMENT OF FLUID PARAMETERS

RELATED APPLICATION

This is a continuation-in-part of U.S. Ser. No. 07/965,193 filed on Oct. 23, 1992 with the same title, now abandoned.

FIELD OF THE INVENTION

This invention is related to optical sensors and materials and methods for making optical sensors. In one aspect, this invention is directed to multiple fiber optic sensor probes for sensing or suitable for sensing and monitoring fluid parameters, including but not limited to physiological blood characteristics such as pH and blood gas concentrations. In another aspect, multiple sensors are used in one catheter-like probe. One aspect of the present invention discloses and describes materials for and methods for making fiber-optic probes useful for measuring and monitoring blood gases, pH, and electrolytes in fluids.

BACKGROUND OF THE INVENTION

Physiological measurement of blood gases and hydrogen ion ( pH ) is very important for a variety of reasons. Myocardial contractility after cardiac surgery is strongly influenced by the acid-base balance. Patients with low cardiac output or with severe pulmonary disease show strong signs of acid-base imbalance due to changes in the peripheral circulation or in ventilation-perfusion relationships. Further, the optical determination or monitoring of blood oxygen and carbon dioxide saturation levels during certain medical procedures, such as critical cardiopulmonary and cardiovascular bypass heart surgery has numerous advantages. Equally important is the physiological measurement of pH in blood or serum along with oxygen for oxygen-heamoglobin dissociation circle and other diseases e.g. sickle cell anemia and malfunctions.

Fiber optic devices for measurement of blood gases, pH, electrolytes, and glucose are well known. Certain prior art sensors usually include an indicator molecule (dye) such as fluorescent or absorption dye which interacts with the component to be sensed or measured. Typically, an indicator, often in combination with an analyte permeable matrix, is a sensing element or a sensor means and is placed on or adjacent to a surface in the light path of the fibers. The interaction between the indicators and the component to be measured or sensed or analyzed is monitored utilizing signals carried by the fibers. Such a probe can be introduced into an artery to measure, depending on the type of dye molecule, various blood parameters such as pH, pCO2, and pO2. U.S. Pat. No. 4,682,895; 5,006,314; 4,974,929; 4,824,789; and European Patent Reference 0,352,610 describe various prior art probes.

It is a major aim of sensor/probe development to combine more than one sensor in a single probe so that a patient is not overtaxed with various probes introduced in his or her arteries. Such a combination or multiple sensor probe may, for example, contain pH, pO2, pCO2, and/or a stabilized element such as thermocouple wire.

SUMMARY OF THE PRESENT INVENTION

The present invention, in one embodiment, discloses an implantable blood gas sensor device and methods and materials for making optical probes with one or more sensors, including but not limited to, multiple sensor probes for measuring blood gases and pH.

This invention discloses, in one embodiment, a drift-free fiber-optic sensor suitable for monitoring, and preferably for continuously monitoring, intra-arterial physiological blood gases and other analytes. One or more analyte permeable matrices or membranes encapsulate an indicator matrix inside a chamber ( cell or cavity ) situated in a fiber optic's light path (see e.g. the devices disclosed in U.S. Pat. No. 5,124,130 which is co-owned with this application and is fully incorporated herein for all purposes and the items and methods disclosed in the application entitled "Optical Sensor For Fluid Parameters" filed on even date Herewith and co-owned with this application, which is also incorporated fully herein by reference and a copy of which is appended hereto and filed herewith as part of this application.) The indicator matrix contains a dye ( indicator molecule ) adsorbed or immobilized on a selective solid surface support or covalently bonded or linked to a selective solid or polymer support, preferably controlled pore glass such as, but not limited to, aminoaryl CPG, average size 5 um particles, commercially available from CPG Inc., or covalently linked to controlled pore glass via methods described in the prior art. In another type of analyte sensing, this support may be silica- gel- based highly porous material such as Lithosphere particles of uniform size ( preferably 10 micron) or Kieselgel ( chromatography grade ) or Chromosorb ( Rohm Haas), polymer such as XAD-4, Dow Sorb (The Dow Chemical Company) and other polymers related to PMMA derivatives. Loading or filling of an indicator matrix is done with a slurry , paste or cement like dough made with a support polymer ( preferably ) or a non-ionic gel like Hydroxy ethyl cellulose (HEC), Hydroxy methyl propyl cellulose (HMPC), Methocel ( from The Dow Chemical Company), Ethocel ( The Dow Chemical Company), Kollidones (BASF,Inc), Dextran, Polyvinyl pyrrolidine (PVP) , Polyethylene Glycols Silicon fluids or Polydimethyl siloxanes or derivatives. A drift-inhibited or a drift-free performance is obtained with such sensor probes having encapsulated indicator molecules with analyte permeable membranes of considerably less than about 20 to 30 um (microns) in thickness.

The gas or analyte permeable membranes or coatings or layers of membranes which are efficiently capable of responding to a target or unknown analyte with a fast response time and specific selectivity are carefully made preparations utilizing polymers such as cellulose acetate, cellulose acetate esters, siloxanes polycarbonate copolymers, polyurethanes, ethyl vinyledine copolymer, silicon and PVC which are carefully cast or filmed from organic polar or nonpolar solvents. Porosity, gas permeability and flexibility of such membranes or films of membranes can be effected or regulated by the minor addition of components like water, methanol, zinc salts, magnesium salts or mixed solvents.

Certain preferred probes or sensors according to the present invention have an opaque or a light protecting cover coating or overcoat. The overcoating provides durability and mechanical strength to inhibit or prevent peeling or falling apart of the membrane inside a conduit, e.g. but not limited to, a human artery during a cardiovascular procedure to monitor blood gases or other analytes in blood. These overcoatings preferably meet the required criterion of permeability to the component or components being sensed by other sensing indicators. These coatings are, preferably, sufficiently permeable to an analyte to be measured or determined so that it can selectively allow the sensing molecule to sense analyte change. This opaque coating can be distributed to cover all the analyte chambers or cells or areas sensitive to indicator molecules. Such opaque coatings may also: prevent outside light from entering into an indicator chamber; reduce migration of molecules; act as a reflector for inside light (e.g. signal in a fiber optic); and provide a uniform physical appearance and strength to a probe.

In certain embodiments of the present invention, sensors are made or manufactured utilizing solvent based film coating/dip coatings in a semi-automatic process with an analyte sensitive indicator or dye molecule covalently bonded or attached to or adsorbed/admixed in a support matrix formulation. This methodology facilitates mass production of the probes. The coatings or membranes can be applied by dipping, spraying or painting the area described on a probe surface.

Solvents used in certain embodiments of the present invention for composition of membranes or coatings are selected in such a way that polymer material or its precursors is completly soluble in the composition. These solvents are preferably non aqueous and may be polar or non-polar organic in nature. Chlorinated and non-chlorinated hydrocarbon solvents may also be used while other oxygen containing hydrocarbon solvents such as ketones and ethers may be used. Methylene chloride, ethylene chloride, acetone, and methanol are particularly useful.

From the standpoint of patient safety ( i.e., danger of infection and damage to blood vessels), the biocompatibility of implantable sensors is a prime consideration in the clinical acceptance of sensor probes. Therefore, a primary goal of in vivo optical sensor probes as disclosed by certain preferred embodiments of the present invention is the incorporation of biologically compatible materials, e.g., but not limited to silicon, siloxanes and urethanes coatings and/or materials which satisfy minimum requirements or preferably exceed standard protocols biocompatibility.

The thickness of the membranes and coatings in certain preferred embodiments according to the present invention are an important factor in producing reliable and quantitative features of permeability and response time. These thickness parameters over the probe sensor body can, preferably, vary uniformly in the range from about 10 to about 20 microns, and most preferably between about 12 to about 15 microns.

In one embodiment of the present invention, a multi-sensor probe has an overcoating application which makes the probe resist blood clot formation or prevents clot build-up during clinical procedures or while the probe is inside a human artery in contact with blood. The effect of such a film or coating on the probe body is to inhibit the adverse effects of having the sensors or probe in the blood stream. Examples of anti-thrombogenic reagents include commercially available Heparine-benzylkonium salt complex ( H-BAC ), Tridodecylammonium salt complex (TDMAC) of heparine, Steara-alkonium salt complex of heparine and film made of derivatized cellulose with long alkyl chains. The films of these reagents are cast from mainly polar solvents such as alcohols except in those cases where a combination of solvents is needed to dissolve the reagent.

It is preferred that a sensor or probe according to the present invention undergo individual sterilization inside a pouch, package or sterile container such as plastic or foil pouch bags, typically accompanied by printed instructions for use. Sterility of the probe or sensor may be confirmed by known irradiation dose of gamma radiations or E-beam exposure. In the present invention gamma irradiation is preferred to avoid residual EtO presence and risk of incomplete sterilization by E-beam. Sensor probes can be packed in fully hydrated condition, especially soaked in an optical validation solution, OVS or a calibration fluid.

A sterilized sensor probe can be easily calibrated by placing the probe in an optical validation solution ( OVS ) and allowing it to equilibriate. After proper equilibrium is reached, the solution pH is allowed to change to two different pH values by bubbling gases and bringing the OVS to known values of $CO_2$ and $O_2$ comparable with blood concentration to permit calibration of each parameter. At this stage the probe is also, preferably, independently tested for $CO_2$ in order to make certain its functionality as a $CO_2$ sensor and not as a misleading alternate pH sensor.

An object of the present invention is to provide a unique, novel, useful, effective, efficient and non-obvious fiber-optic sensor and probe and methods for making them.

Another object of the present invention is the provision of chemistries useful in such methods and in such sensors and probes.

A further object of the present invention is the provisions of methods for formulating, preparing, and casting films or membranes over chambers holding indicator molecules, preferably in the form of paste or gels.

BRIEF DESCRIPTION OF THE DRAWINGS

The advantages and useful features of the present invention will be more fully understood from the following description of the preferred embodiments, taken into consideration with the accompanying drawings. The attached drawings illustrate preferred embodiments of the invention and are therefore not to be considered limiting of its scope, for the invention may admit to other equally effective equivalent embodiments.

DETAILED DESCRIPTION OF THE INVENTION

In certain preferred embodiments an optical probe sensor according to this invention is useful in the measurement of physiological blood gases ( $pCO_2$, $pO_2$) and pH (hydrogen ion concentration); but such probes are also useful in the measurement of other physiological phenomenon ( such as electrolytes and glucose ) which exhibit similar behavior.

U.S. Pat. No. 5,124,130 describes the making of an optical probe with plastic fibers using a "bend" design. The fiber-optic sensor probe, according to the present invention, has optical gaps or chambers, formed in the optical fibers, which can be filled with a desired chemical indicator. These indicators can be covalently bonded to a solid support and matrix via chemical reaction and/or immobilized on polymers of choice or on an inert support such as controlled pore glass (CPG) or silica gels. These indicators can also be adsorbed on solid polymer supports. These indicator molecules can be held in place within the optical gaps in the form of a gel or paste slurry made with soluble polymeric compounds or insoluble polymer fluids such as silicon or siloxanes and their derivatives. The selective permeable membranes are used to encapsulate the indicator or cover the indicator inside the chambers to prevent loss of the indicator compound or contamination by undesired chemical species in the environment. The application of a second membrane or overcoating (usually opaque in nature) is applied over the permeable membrane to prevent the loss of light, reflection of light inside the chamber and cross contamination by outside light entering into a chamber and giving false signals. Finally, an anti-thrombogenic coating or anti-clot coating is applied over the entire probe body surface. The use of such coatings provide additional strength to the probe sensor during clinical procedures and prevent clot formation and deposition of any foreign materials such as blood proteins on the surface of probe. After proper curing of all the materials, especially membranes, the fiber-optic probe can be stored in hydrated condition for future use. This hydration is supplied by immersing the probe in a container of calibration fluid (OVS).

Figure 1:
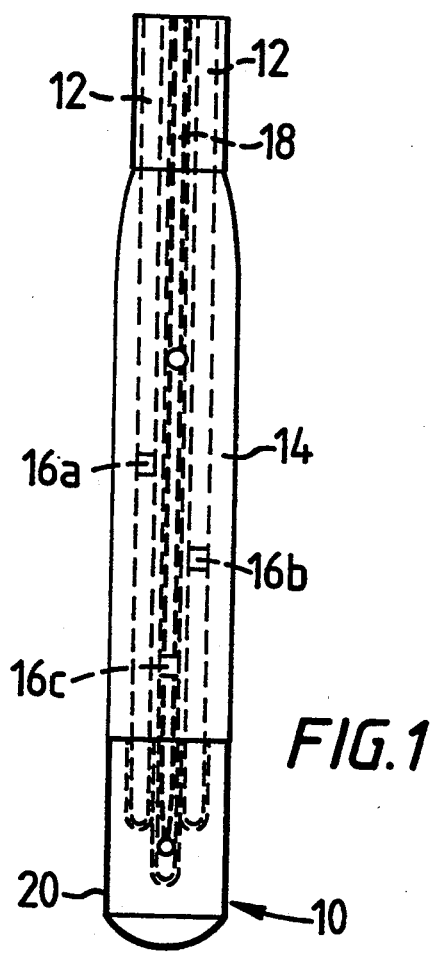
FIG. 1 is a schematic view of a probe showing fibers, potting material, chambers, thermocouple wire, polyimide tube and a mark.

The choice of materials to be used in making the fiberoptic sensor probe (FIG. 1) is greatly influenced by the need to simultaneously satisfy many requirements. Most importantly, the indicator support matrix (FIG. 2) bonds or immobilizes the indicator dye molecules effectively without leaching over the period of time of assays. Otherwise, signal drift will result from leakage or creeping of indicator molecules, especially water soluble molecules like phenol red and related acid-base indicators and soluble luminescent dye molecules. Preferably, water soluble indicators are covalently bonded to a component or solid support matrix or a dyed support is overcoated or encapsulated with water insoluble coatings or fluids such as silicons. The resulting sensor probe made in this way has reduced drift or is drift free, that is, there is little or no detectable leakage or diffusion of indicator molecules from the matrix (FIG. 2) in the environment of use over the time period of the assay or measurement.

Figure 2:
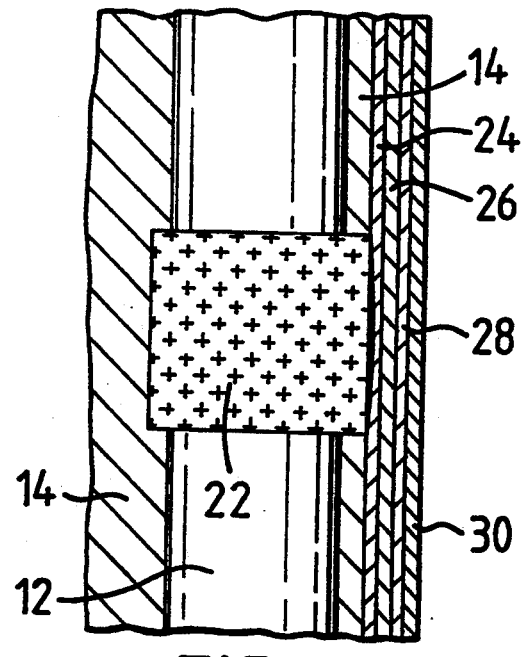
FIG. 2 is a perspective view of the chamber, cell or cavity for indicator loading and encapsulation by membranes.
Figure 3:
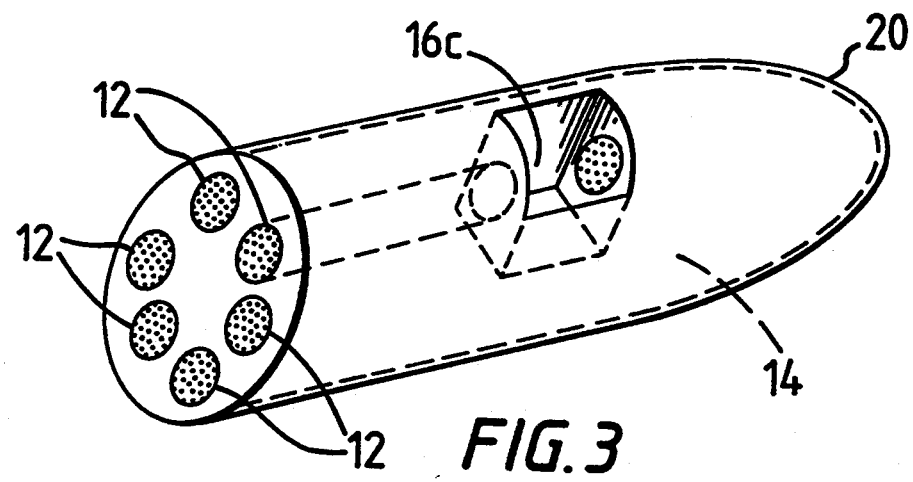
FIG. 3 is a cross-section view of a bundle of optical fibers inside the potting material showing an optical chamber.

Referring to FIG. 2, the indicator matrix or support is, preferably, able to permit the free passage in and out of the analyte substance or component, that is, the support should be analyte permeable. For physiological applications in which the analyte is dissolved or dispersed in aqueous solution, the support for an indicator is, preferably, hydrophilic as well as porous to the analyte component (such as pH and pCO2) and in, certain other cases such as pO2 the support matrix is, preferably, highly permeable to oxygen gas and allows the analyte to come in full contact with the indicator molecules. However, it is important, preferably, to control the undue swelling of the support matrix by regulating the hydrophilicity. These support matrices are preferably large enough to allow the passage of an analyte of interest, but sufficiently small enough to preclude passage of unwanted substances such as blood proteins, that might chemically or physically interfere with the measurements.

It is preferred that the support matrix be optically clear and that the refractive index of the matrix (FIG. 2) be reasonably well matched to that of the optical fiber core and to that of the potting material in order to minimize light scattering effects. In addition, it is preferred that the support matrix not shrink or crack upon drying or rehydration. The matrix should retain its rigidity and strength during use in blood vessels.

In one preferred embodiment of a probe, according to this invention, a first analyte indicator is sensitive to pH concentration. In a second embodiment the first analyte indicator is sensitive to carbon dioxide concentration. In a third embodiment, the second analyte indicator is sensitive to oxygen concentration, alternatively in both the first and second embodiments, a second analyte indicator is sensitive to oxygen concentration. Hydrophilic matrix material for a pH and pCO2 optical sensor can be an ion permeable polymer material which is compatible with the other components of the system. Examples of such materials include Hydroxy propyl cellulose (HPC), Hydroxy ethyl cellulose (HEC), Hydroxy propyl methyl cellulose (HPMC), Kollidones or Povidones, Hydrogels, Polyacrylamide and PVA and the like. On the other hand hydrophobic or solid support materials include Lichrospheres, Silica gels, fumed silica, XAD-4 (Amberlite from Rohm-Haas) or the like.

In embodiments in which the indicator molecule is water soluble and adsorbed on a solid surface such as in an oxygen probe according to the present invention, the solid support is preferably encapsulated or coated uniformly with a water repellent polymer matrix to prevent leaching or loss due to slow solubility. Such materials are preferably gas permeable and water insoluble; e.g. silicon fluids, dimethylsiloxanes and their derivatives, polymer elastomers, RTV silicons, silicon adhesives and sealants (UV cure and room temperature cure).

As noted earlier, certain preferred embodiments of the present invention include optical probes with a certain dye, dye support, dye support matrix and envelopes or membranes. A suitable dye, preferably, has the following characteristics:

1. It is capable of excitation by visible wavelengths which can be transmitted by plastic optical fibers of the type which are unbreakable, when subjected to sharp bends, are highly flexible and which can be used for making easy optical coupling.

2. It is stable to light and has adequate resistance to aging.

3. It is non-toxic.

4. Oxygen sensitive dyes have sufficient oxygen quenching sensitivity with long mean lifetime of the excited state as required to obtain measurements to the nearest ~1 mmHg/pO2.

5. Absorption based dyes provide a good working range of pH values (6.7–7.8) and these have pKa close to the working pH range.

6. It is stable under ordinary, UV and gamma radiations.

There are certain aspects of preferred dyes. Many UV excited dyes have a high quenching sensitivity, but the requirement of visible light excitation is difficult to meet. An example of such a dye is pyrelene dibutyrate. Other suitable dyes are reported in the references given herein. In this illustrated embodiment of the pO2 probe sensor (FIG. 1) the use of metal complexes as luminescent indicators are considered the best choice for their use. In one preferred embodiment, the present invention uses an oxygen sensitive fluorescent dye of tris(1,10-phenanthroline)Ru(II) chloride (obtained from Aldrich) or tris(4,7 diphenyl 1,10 phenanthroline) ruthenium chloride. In other embodimnets, oxygen sensitive dyes may be made of any salt of the tris(1,10-phenanthroline)Ru(II) cation. In particular, the anion used can be taken from the group including thiocyanate, perchlorate, hexafluorophosphate, tetrafluoroborate and/or any other halide. In other embodiments, oxygen sensitive fluoroscent dyes are made of any salt of a transition metal complex of ruthenium ion having ligands such as 2,2'-bipyridine or derivatives, 1,10-phenanthroline and substituted derivatives. Preferably, the transition metal cation should be taken from the group including ruthenium(II), osmium(II) and rehenium(III). Protocols are set forth below in example (1) for making a $pO_2$ indicator complex attached to solid support and support matrix.

In one preferred embodiment of the present invention for pH and $pCO_2$ sensor probes, use of absorption based dyes are selected from a group of molecules such as phenol red (commercially available from Sigma Chemical Co.), bromothymol blue (commercially available from Sigma Chemical Co.) and derivatives. The required indicator molecule is selected to respond optically in the presence of the targeted analyte component when immobilized on the indicator solid support and converted into matrix paste. The response of the indicator is, preferably, highly specific for the targeted analyte in order to minimize interferences and background signal noise. For continuous monitoring, as in certain embodiments of the present invention, the reaction or response between the indicator molecule and the analyte is reversible as well as sensitive and specific. The selected indicators suitable to have such properties are used in this invention.

It is preferred that an indicator's selectivity, specificity and reversibility of its typical response to the analyte not change after it is covalently bonded or immobilized on a solid or polymer surface. Also the indicator preferably does not lose its analyte sensitive sites after immobilization. Also, steric hindrance to the analyte specific sites is, preferably, minimized. The indicator molecule is, preferably, therefore uniformly bound to the solid support in a site-specific manner that preserves the optical response behavior of the molecule to the analyte.

For this purpose, aminoarylated controlled pore glass (C.P.G. Inc., 5 micron mean size) is preferred and employed to covalently link the indicator molecule (phenol red or bromothymol blue). Other well suitable absorption dyes such as chlorophenol red, bromocresol purple and nitrophenol can also be used. Alternatively, unmodified controlled pore glass (Pierce, CPG or Fluka) is used to bond indicator molecules by treating the glass with known funtionalized groups such as y-APTSi (3-amino propyltriethoxysilane) and making it amino functional (Baldini et al). The free arylamino group is then reacted with the indicator molecule of choice, for example by diazotization and coupling with indicator molecules such as phenol red that have strong electron releasing groups. One type of this method is provided in example (2).

In another embodiment of the present invention, the fluoroscent dye molecule·tris(1,10-phenanthroline) ruthenium (II) chloride (or tris(4,7 diphenyl 1,10 phenanthroline) ruthenium chloride) is adsorbed on a solid support such as lichrospheres (10 Micron) from its solution. To provide a good gas permeable water repellent barrier to indicator molecules adsorbed on the solid support, a silicon fluid such as polydimethylphenylsiloxane, silicon elastomer such as Dow's MDX 4210, uncured polydimethylsiloxanes (high viscosity) or RTV silicon or substituted siloxane was mixed or smeared to obtain a uniform paste or slurry (support).

In the preferred embodiment, an uncured silicon elastomer, preferably Dow MDX 4210 (part A) or silicon fluid (Dow Corning 556 cosmetic grade) is the choice of interest. Similarly, with a pH and $pCO_2$ probe sensor according to the present invention, covalently bound indicator molecules are encapsulated or uniformly made into a paste or slurry with soluble hydrophilic polymer from a group of materials which include Hydroxy ethyl cellulose, Hydroxyproyl cellulose, Kollidone (PVP), Cellulose, methocel, and hydrogel. The preferred matrix is hydroxy ethyl cellulose (Polysciences, Inc. and Fluka) which provides a stable and uniform slurry of the indicator molecules for faacilitated loading of indicator inside a chamber.

It is within the scope of the present invention to use several polymers for the unique design of the disposable sensor probe. For example, the polymer may, preferably, be from a group of materials including Polyurethane, Cellulose Acetate esters, Polycarbonate, Polyvinyl carbonate, Polyvinyl butyrate, Silicon rubber and Polyphenylsilsequioxanes. In general, most of the polymers can be used provided they are easily soluble in the solvents which will not attack the optical fibers used and cured potting materials such as ELC 4481 (Electrolite Corporation), DeSolite 3471-2-33(DeSoto, Inc.), FMD-8 (Loctite Corp.), and 186 M (Dymax Corp.) or Luxtrac (I.C.I. Corp.).

In certain preferred embodiments of the present invention, it is preferred to provide a suitable and highly responsive gas-permeable solution or fluid impermeable envelope or membrane over the $pO_2$ and $pCO_2$ chambers to protect the indicator complex slurry inside the chamber as illustrated in FIG. 2. Simultaneously, the pH chamber is enveloped or covered by a highly selective and specific membrane permeable to hydrogen ion, but impermeable to other substances such as proteins (illustrated FIG. 2). In another preferred embodiment of this invention, a second envelope or selective membrane cover is applied over the $pCO_2$ and $pO_2$ chamber area to ensure that these sensors are fully gas permeable and water or solution impermeable. This is illustrated in FIG. 2. By applying double membranes over the $pCO_2$ and $pO_2$ indicators serious problems are avoided with the sensor that it is only. Sensitive to $CO_2$ molecules, but not cross-sensitive to hydrogen ion (pH interference). The present invention offers a full solution for this problem in that the used membranes are only permeable for gas molecules, but not for hydrogen ions.

The determination of $pCO_2$ is carried out indirectly by measuring the change in pH of a calorimetric pH indicator phenol red in this case) in the presence of a bicarbonate buffer medium being in equilibrium with the local $pCO_2$. Therefore, for maximum linearity, the pH of the gel or slurry is adjusted to be equal to the dye pKa (acid dissociation constant) at the midpoint range of $pCO_2$'s to be measured. In the present invention, a bicarbonate concentration of 35 mmole which provides an effective range for a nominal $pCO_2$ of 40 mmHg is used. Enough salt (sodium chloride) is added to make the medium isotonic. The success of the $pCO_2$ sensor probe also depends, besides other factors, on the stability of bicarbonate buffered gel inside the sample chamber. The use of gamma radiation during probe sterilization should result in some degradation of bicarbonate with apparent loss of sodium bicarbonate. To avoid this, an antioxidant reagent (conc. 0.1%) can be premixed in the bicarbonate buffer before its use. However, in certain preferred embodiments of the present invention the use of any antioxidant is carefully avoided, but is not ruled out for other embodiments.

Preferred materials for certain membranes according to the present invention include Dimethylsiloxane bisphenol A carbonate copolymer ( e.g. from Oxygen Enrichment Co. Product MEM 220), Polyurethane ( Tecoflex, solution grade SG-80A from Thermedix), Cellulose Acetate Ester( Eastman Kodak, product 398-10), Ethylene-vinyl acetate copolymer (Scientific Polymer Products, Inc.), and Polycarbonate (Aldrich Chemical Co.). Certain preferred embodiments of the present invention utilize solvent based film coatings or membrane techniques to make sensor probes. This process facilitates mass production of fiber optic sensor probes. The sensors can be simultaneously and uniformly coated by dipping, spraying or otherwise painting the probe body or indicator covering area. In another embodiment of present invention, an opaque coating or membrane which is gas and hydrogen ion (pH) permeable is made using opaque materials, e.g. but not limited to $TiO_2$ powder (commercially available from Aldrich or Whittaker, Clarke and Daniels, Inc. );, Graphite powders ( The Asbury Graphite Mills, Aldrich and Johnson Mathey); and carbon powders ( Aldrich, Alfa and Lancaster Dispersion ). The most preferred material is graphite powder.

Such overcoatings enhance the performance of probes in several ways. The overcoating serves as a protective membrane over the sensors to isolate the optical indicator from the environment which is being measured or sensed. Also the sensor is optically isolated from outside light or from a second sensor located in the vicinity of a first sensor. Additionally, such overcoatings provide a suitable surface on which further material can be located, for example, a film or coating of an anti-thrombogenic reagent.

The opaque coating or membrane is applied on the whole surface area over an indicator, partially covered area, or simply covering the area scanned of chambers where the coating only protects the indicator complex or molecules. Our such coating is based on cellulose acetate material modified for its porosity and strength. These coatings are water insoluble and mechanically strong and smooth on a surface with good permeability. It is preferred that these coatings are made from material which is biocompatible and which does not lack compatibility with body fluids such as blood. Such coatings are stable, strong, biocompatible and do not leach anything during the course of an assay.

Sterility of the sensor probes is achieved by known irradiation by gamma radiation (2.5 mrad ). Gamma sterilization is preferred for avoiding the risk of residual EtO presence ( in case EtO sterilization is used ) and due to the hydrated nature of the sensor. Sensors are preferably packaged in hydrated condition for easy handling for gamma sterilization and calibration. The sensors are also, preferably, individually packaged in suitable containers such as foil pouches, typically accompanied by printed instructions for their use.

One embodiment of a multiple sensor according to this invention is stored or packaged in a container filled or saturated with OVS ( optical validation solution ). The system, preferably, incorporates one prepacked container contaning calibration solution ( OVS ) having known values of the parameters to be measured by the system or sensor. This calibration solution has different known values for each of the measured parameters ( pH, pCO2, and pO2) at two different gas levels (for example, Gas #1 and Gas #2; gas #1 contains 8% carbon dioxide; 3% or 7% oxygen; and balance nitrogen;, gas #2 contains 3% carbon dioxide; 25% oxygen; and balance nitrogen) to allow the sensor to be calibrated on a two point basis. For the purpose of reference the solution contains within the probe container an additional container with a second optical calibration solution - (OVS). Each container contains a sufficient quantity of this solution to allow the sensor to be calibrated several times ( if needed ) before insertion into the human body.

In one preferred embodiment of the present invention, the pO2 probe need not be hydrated and does not require a hydration condition for packaging. As a part of a multiple probe sensor, a three sensor probe is, preferably, kept hydrated. The calibration of the probes is achieved by placing the multiple sensor probe in OVS (calibration solution ) and letting the probe equilibriate with Gas #1 and recording the blood gas data on a blood gas analyzer. In the second step, the multiple sensor probe is equilibriated in the same solution, but with a different gas level of saturation. In this case Gas #2 is bubbled through the same solution and the blood gas data and pH are recorded on a blood gas analyzer. Comparison of the known values of pCO2 and pO2 content of the OVS at different gas equilibriums with normal blood gas concentrations of interest permit calibration of each parameter.

One embodiment of this invention provides compositions of a calibration solution herein called Optical Calibration Solution (OCS) or Optical Validation Solution (OVS). The solutions are a stable, homogeneous liquid standard or control solution which provide for the measurement of parameters such as blood pH, PCO2 and pO2 for in vivo monitoring. This calibration solution, in one embodiment, comprises an aqueous solution buffered to a pH of about 6.8 to about 7.8 and contains sufficient bicarbonate ion to provide a pCO2 from about 15 mmHg to about 90 mmHg after subsquent equilibrium with desired levels of gas mixture and a pO2 of about 20 mmHg to 300 mmHg. this solution is useful for a blood gas control solution in the physiological condition. In order to provide the desired pH for the respective normal acidosis and alkosis condition, a buffer material should be selected which has pKa close to the working range of pH. Several useful buffer materials for providing an acceptable preferred pH condition in the calibration solution are: TES ( N-tris-(hydroxymethy)-methyl-2-aminoethanesulfonic acid ) which has a pKa of 7.16 at 37° C.; TRICINE( N-tris-(hydroxymethyl)-methylglycine) which has a pKa of 7.79 at 37° C.; MOPS (3-(N-(morpholino)- propanesulfonic acid) which has a pKa of 7.01 at 37° C.; and HEPES(N-2-hydroxyethylpiperazine-N'-2-ethanesulfonic acid) which has a pKa of 7.31 at 37° C. These and other such buffers including the sodium salts are described by Good et al. ( Biochemistry Vol. 5 (1966) and Ferguson et al. ( Analytical Biochemistry, Vol. 104 (1980).

To prevent any bacterial or fungus growth as well as to increase the shelf life of optical validation solution (OVS), a preservative can be added during preparation of the solution. Several useful materials with antibacterial and antifungus properties include ProClin-300 (Rohm & Haas), Sodium azide, Benzyl alcohol, Kathon ( Rohm & Haas ), and mercury salts. In the present embodiment of this invention, the most preferred material is ProClin-300.

A representative example of OVS or OCS along with its preferred composition is given in Table 1. This composition is effectively a blood facsimile and has the following parameters ( Table 2):

TABLE 1

| Compound | Conc. (mmol/L) | grams/liter |
|---|---|---|
| 1. NaCl | 100 | 5.840 |
| 2. KCl | 4 | 0.298 |
| 3. NaHCO$_3$ | 25 | 2.100 |
| 4. MgCl$_2$.6H$_2$O | 1 | 0.203 |
| 5. Na$_2$HPO$_4$ | 1 | 0.141 |
| 6. CaCl$_2$.2H$_2$O | 2 | 0.294 |
| 7. TES | 15 | 3.440 |
| 8. NaOH | 1N | 4.0 ml. |

TABLE 2

| Gas mixture | pH (units) | pCO$_2$ (mmHg) | pO$_2$ (mmHg) |
|---|---|---|---|
| Gas#1 (3% O$_2$) | 7.14–7.26 | 53–59 | 35–55 |
| Gas#1 (7% O$_2$) | " | 55–60 | 45–55 |
| Gas #2 | 7.50–7.62 | 20–26 | 165–195 |
| No Gas | 7.10–7.37 | 40–70 | 150–180 |

The packaged calibration solution (OVS) posesses an excellent stability and a long term shelf life, When properly stored at room temperature and atmospheric pressure, the possibility of outgassing from the liquid to form gas bubbles within the container sealed in a foil pouch bag is significantly reduced or eliminated.

EXAMPLE 1 - Oxygen Indicator 0.246 gm (3 mmol/L ) of Ru(1,10-phenanthroline)3Cl2 obtained from Aldrich Chemical Co. was dissolved in 100 ml of double distilled water. To this solution 1.0 gm of Lichrospheres (10 um size ) obtained from E. M. Science was mixed and contents stirred for 2–3 hrs. After filtration the dyed lichrospheres powder was dried in an oven at 100° C. 0.1 gm of the dyed material was uniformly mixed (smeared) with 0.255 gm of uncured silicon elastomer ( Dow MDX 4210 Part A) until a consistent uniform paste was obtained.

EXAMPLE 2 - pH & Carbon Dioxide Indicator 0.40 gm of phenol red dye ( cell culture grade obtained from Sigma Chemical Co.) was dissolved in 40 ml of 2N HCl. To this cold solution 1.0 gm of controlled pore glass ( CPG Inc.) was mixed and the contents stirred for 10 minutes and then cooled to −2° C. for 2 hours. After this 0.64 gm of sodium nitrite ( Sigma Chemical) was slowly added under slow vaccum. After stirring for 10 minutes the solution was brought to −2 degrees C. and maintained at this temperature for 2–3 hours. After this time the indicator glass was filtered through a 3 um (micron) polycarbonate filter and the solid was washed with slightly basic distilled water until washings showed no color as tested by spectrophotometer. The filtered solid was dried first in air then in an oven at 60–70 degrees C. for 12 hrs.

Preferred support media or matrices for indicator complexes for pH and pCO2 probes (made prior to mixing with a solid indicator) include the following:
 (a) pH support media: 0.2 gm of hydroxyethyl cellulose obtained from Polysciences Inc., was dissolved in a vial with 20 ml of optical calibration solution. The contents were mixed until no undissolved material remained in the vial.
 (b) pCO2 support media: 0.2 gm of hydroxyethyl cellulose obtained from Polysciences Inc. was dissolved in a vial with 20 ml of 35 mmolar bicarbonate buffer ( obtained by dissolving 0.336 gm of sodium bicarbonate( Sigma cell culture grade) and 0.24 gm of sodium chloride(Sigma cell culture grade) in 100 ml of tissue culture grade water.). The contents were mixed until no undissolved material remained in the vial.
 (c) To obtain the pH indicator complex, 0.1 gm of indicator dyed glass (as made in this example) was uniformly mixed with 0.4 gm of pH support media. Similarly, pCO2 indicator complex was made using 0.1 gm of indicator dyed glass with 0.4 gm of pCO2 support media.

EXAMPLE 3 - pH Membrane 0.80 gm of magnesium perchlorate( GFS Chemicals) was easily dissolved in 15 ml of pure methanol( Sigma ). To this solution 20 ml of methylene chloride ( Fisher ) was added and to the whole contents 2.2 gm of cellulose acetate ester powder ( Eastman Kodak, product 398-10) was dissolved slowly for 6 hrs until a clear homogeneous viscous solution was obtained.

EXAMPLE 4 - Hydrophobic Gas-Permeable Patch Membrane Material 1.05 gm of dimethylsiloxane bisphenol A polycarbonate copolymer resin ( Oxygen enrichment Co.) was dissolved in 15 ml of ethylene chloride solvent ( Protein sequencing grade from Sigma), producing a clear viscous solution.

EXAMPLE 5 - Gas Permeable Dip Membrane 0.72 gm of polyurethane resin ( grade Tecoflex SG-80A obtained from Thermedix ) was dissolved in 20 ml of methylene chloride solvent (Fisher), producing a clear viscous solution.

EXAMPLE 6 - Opaque Coating 0.15 gm of magnesium perchlorate ( GFS Chemicals) was dissolved in 12 ml of pure methanol ( Sigma). To this was added 19 ml of methylene chloride and the mixtuire was used to dissolve 1.2 gm of cellulose acetate ester( Eastman Kodak product 398-10). for 6 hrs. After a uniform solution was obtained, 2.4 gm of graphite powder( Asbury graphite Mills) was mixed into the solution and whole contents were stirred for 6 hrs for complete dispersion and uniform mixing, producing a black viscous material.

EXAMPLE 7 - Opaque Coating

White overcoating membrane was made similar to pH membrane as described in example 3 except 2.0 gm of TiO2 powder. ( Aldrich Chemical Company) was added to the solution in a container and its contents were mixed together for 6 hrs for uniform mixing and consistent dispersion of the powder, producing a white opaque mixture.

EXAMPLE 8 - Anti-thrombogenic Coating 40.0 ml of H-BAC ( heparine complex of benzalkonium chloride obtained from Polysciences Inc., product No. 18332) was slowly evaporated to near dryness in an oven at 70 degrees C. A sticky mass was produced and to it 30 ml of pure methanol was added and the resulting mixture was stirred for 6-8 hrs until the residue dissolved completly, producing a clear mixture. Alternate coatings include TDMAC-Heparine( Product No. 03813, Polysciences), S-BAC-Heparine (Stearyldimethylbenzylammonium complex with heparine obtained from Bentley/Baxter) and Hydrogels.

EXAMPLE 9 - Coating Application Method

A thin film or layer of coating or membrane is applied to a sensor to cover indicator complex chambers either by applying membrane material or by dipping the probe into a solution of membranes. After the coating is applied, the solvent is allowed to evaporate. In some cases the coating is cured under humidity environment for several hours. The integrity and strength of the coating is tested independently for its adhesion, mechanical stability, peeling and functionality.

EXAMPLE 10 - Coating Application Method

In a multi-sensor probe having three chambers such as pH, pCO2 and pO2 indicator complex chamber, one on each fiber, the indicator complexes of examples 1 and 2 are used to fill or load the chambers. Next a thin film or patch of specific membrane or coating is applied on the area of each chamber. A hydrophobic gas permeable membrane is then applied on the pCO2 and pO2 chambers area, preferably by a dipping technique. In the next step, the sensor body or probe is dipped in a hydrophilic membrane which covers all three chambers. Preferably an anti-thrombogenic coating or membrane is applied on the surface of sensor probe. After proper curing the probe is immersed in an optical validation solution (OVS) for storage, for further handling, and for testing purposes.

In another method according to the present invention for producing a dry oxygen indicator, about 0.0319 grams of an oxygen dye compound (e.g. 4,7 diphenyl 1,10 phenanthroline) is placed in a clean 30 milliliter vial. About 10 ml of methylene chloride is added to the vial dissolved with an autoshaker. Then about 1 gram of a solid support matrix (as previously described) is added to the vial which is closed tightly with a cap. The vial is stirred on the autoshaker, preferably for at least 4 hours. The vial's contents is then filtered through polycarbonate filter paper (e.g. 3 micron paper) and the filtrate is dried in an even at about 60 to 70 degrees C. for about 12 hours.

In conclusion, therefore, it is clearly seen that the present invention and the embodiments dislosed and described herein are well adapted to carry out the objectives set forth herein. Certain changes and modifications can be made in the methods and materials without departing from the scope and spirit of this invention. It is equally realized that certain changes are possible and it is further intended that each of the following claims is to be understood and considered as referring to all the equivalent elements or steps for achieving substantially the same results in the same or equivalent manner. It is intended to cover this invention broadly in whatever form or manner its principles may be utilized. The invention in which an exclusive property or privilege is claimed is stated in the claims that follow:

We claim:

1. An analyte sensor system for a fiber optic probe, the analyte sensor system comprising
    two optical fibers comprising a first optical fiber and a second optical fiber, each optical fiber having two ends with an end of the first optical fiber having an optical fiber face opposed to an optical fiber face of an end of the second optical fiber, the two optical fiber faces spaced apart from each other,
    a cavity in the fiber optic probe between the two opposed optical fiber faces,
    an indicator matrix disposed in the cavity in a light path across the cavity between the two opposed optical fiber faces, the indicator matrix containing indicator molecules on a support, the indicator molecules for indicating a specific analyte,
    a membrane covering the indicator matrix in the cavity, the membrane disposed over the cavity on an exterior of the fiber optic probe, the membrane accessible by the specific analyte from the fiber optic probe's exterior, the membrane selectively permeable to the specific analyte, and
    the support comprising controlled pore glass particles.

2. The analyte sensor system of claim 1 wherein the controlled pore glass particles are aminoarylated pore glass.

3. The analyte sensor system of claim 1 wherein the controlled pore glass particles are about five microns in size.

4. The analyte sensor system of claim 1 further comprising
    a plurality of four or more optical fibers each with an end with an optical fiber face spaced apart from and opposing an optical fiber face of an end of another optical fiber,
    a cavity in the fiber optic probe between pairs of opposed optical fiber faces,
    an indicator matrix disposed in each cavity in a light path across the cavity between the two opposed optical fiber faces, the indicator matrix containing indicator molecules on a support for indicating a specific analyte,
    a membrane covering the indicator matrix in each cavity and disposed over the cavity on an exterior of the fiber optic probe, the membrane accessible by the specific analyte from the fiber optic probe's exterior, the membrane selectively permeable to the specific analyte, and
    the support for each indicator matrix comprising controlled pore glass particles.

5. The analyte sensor system of claim 1 wherein the membrane is cellulose acetate ester.

6. The analyte sensor system of claim 1 wherein the membrane is polyurethane.

7. The analyte sensor system of claim 1 wherein the membrane is a silicon copolymer derivative.

8. The analyte sensor system of claim 1 wherein the membrane is coated with an anti-thrombogenic coating.

9. An analyte sensor system for a fiber optic probe, the probe having at least one optical fiber, the analyte sensor comprising
    two optical fibers comprising a first optical fiber with two ends and a second optical fiber with two ends,
    an end of the first optical fiber having an optical fiber face and spaced apart from an optical fiber face of an end of the second optical fiber, a cavity in the fiber optic probe between the two opposed optical fiber faces, an indicator matrix disposed in the cavity in a light path across the cavity between the two opposed optical fiber faces, the indicator matrix containing indicator molecules on a support, the indicator molecules for indicating a specific analyte, a membrane covering the indicator matrix in the cavity, the membrane disposed over the cavity on an exterior of the fiber optic probe, the membrane accessible by the specific analyte from the fiber optic probe's exterior, the membrane selectively permeable to the specific analyte, and the support comprising a silica-gel-based porous particulate material with a particle size of about 10 microns.

10. The analyte sensor of claim 9 wherein the particulate material is lichrospheres.

* * * * *